United States Patent
Spanier et al.

(10) Patent No.: US 9,669,142 B2
(45) Date of Patent: Jun. 6, 2017

(54) INTRAVASCULAR ROTARY BLOOD PUMP

(71) Applicant: ABIOMED EUROPE GMBH, Aachen (DE)

(72) Inventors: Gerd Spanier, Aachen (DE); Thorsten Siess, Aachen (DE); Frank Kirchhoff, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 0 days.

(21) Appl. No.: 14/396,708

(22) PCT Filed: Apr. 25, 2013

(86) PCT No.: PCT/EP2013/058642
§ 371 (c)(1),
(2) Date: Oct. 23, 2014

(87) PCT Pub. No.: WO2013/160407
PCT Pub. Date: Oct. 31, 2013

(65) Prior Publication Data
US 2015/0141842 A1    May 21, 2015

(30) Foreign Application Priority Data
Apr. 27, 2012   (DE) .................. 10 2012 207 049

(51) Int. Cl.
*A61M 1/10*    (2006.01)
*A61B 5/0215*  (2006.01)
*A61M 1/12*    (2006.01)

(52) U.S. Cl.
CPC ......... *A61M 1/101* (2013.01); *A61B 5/02154* (2013.01); *A61M 1/125* (2014.02); *A61B 2562/0247* (2013.01); *A61M 2205/103* (2013.01); *A61M 2205/3306* (2013.01); *A61M 2205/3331* (2013.01); *A61M 2205/3344* (2013.01); *A61M 2205/3351* (2013.01);
(Continued)

(58) Field of Classification Search
CPC .......... A61B 5/026; A61B 2017/00243; A61B 5/0031; A61B 2562/0247; A61B 5/0215; A61B 5/6876; A61B 5/021; A61B 5/036; A61M 1/101; A61M 1/125; A61M 1/122; A61M 1/1086; A61M 1/12; A61M 2210/125; A61M 1/1012; A61M 2230/30; F04D 13/06; F04D 29/18; F04D 3/00
See application file for complete search history.

(56) References Cited

U.S. PATENT DOCUMENTS 5,645,531 A   7/1997  Thompson et al.
5,911,685 A   6/1999  Siess et al.
(Continued)

FOREIGN PATENT DOCUMENTS

EP   1911484 A2    4/2008
WO   WO-00/37139 A1   6/2000
(Continued)

*Primary Examiner* — Deborah Malamud
(74) *Attorney, Agent, or Firm* — White & Case LLP

(57) ABSTRACT

An intravascular rotary blood pump possesses a catheter (10), a pumping device (50) fixed distally to the catheter (10) and at least one pressure sensor (30; 60) firmly connected to the pumping device (50) and having a pressure-sensitive area (32) which is exposed to the surroundings and aligned orthogonally to the general longitudinal axis of the blood pump.

14 Claims, 4 Drawing Sheets

Figure 1:
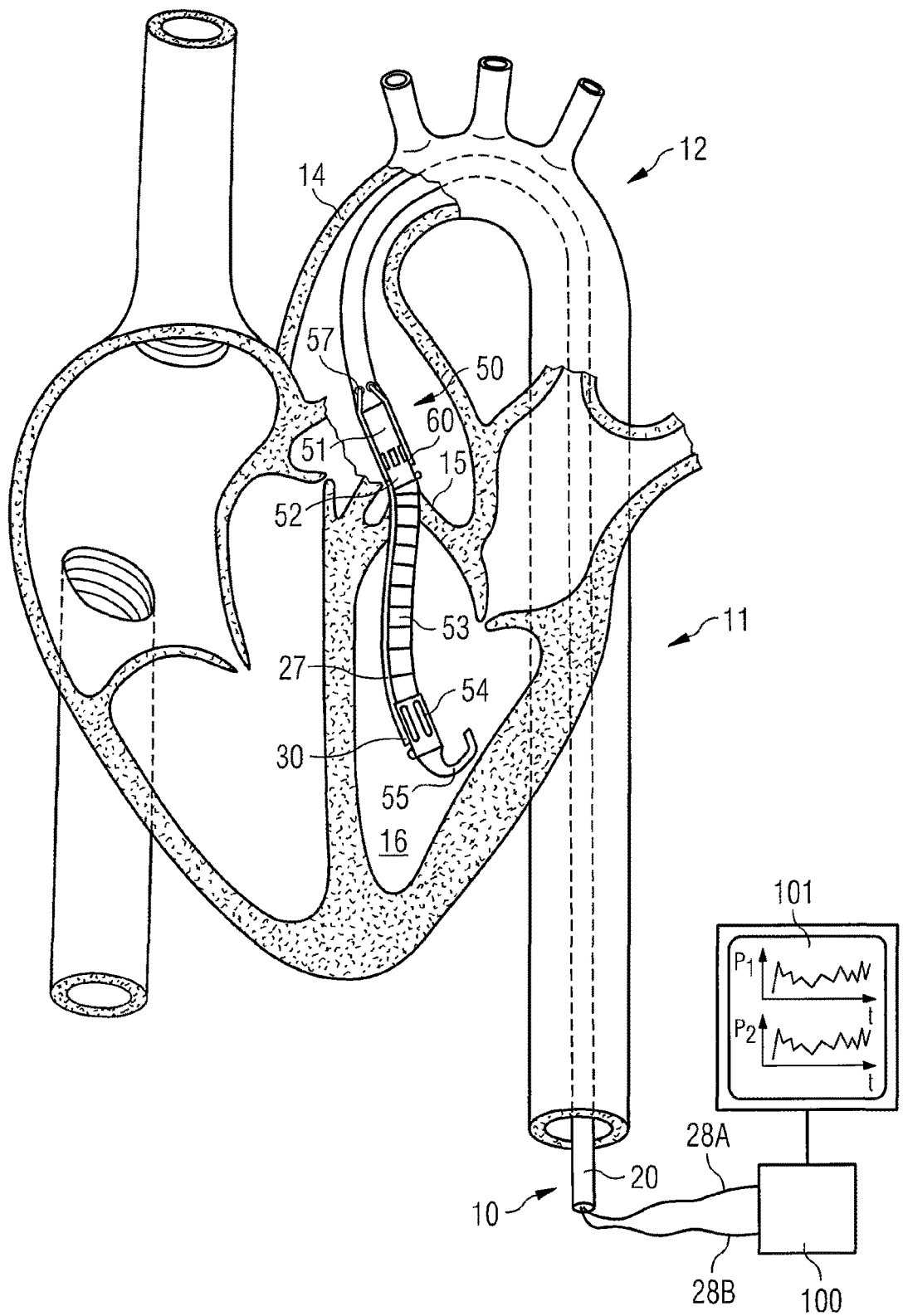

(52) U.S. Cl.
CPC ............ *A61M 2205/3355* (2013.01); *A61M 2210/125* (2013.01); *A61M 2210/127* (2013.01); *A61M 2230/005* (2013.01); *A61M 2230/30* (2013.01)

(56) References Cited

U.S. PATENT DOCUMENTS

| | | | |
|---|---|---|---|
| 5,964,694 A * | 10/1999 | Siess | A61M 1/101 415/900 |
| 6,176,822 B1 | 1/2001 | Nix et al. | |
| 6,398,738 B1 | 6/2002 | Millar | |
| 2001/0051030 A1 | 12/2001 | Hofner | |
| 2003/0187322 A1 | 10/2003 | Siess | |
| 2009/0074367 A1 | 3/2009 | Shinoski et al. | |
| 2010/0241008 A1 | 9/2010 | Belleville et al. | |

FOREIGN PATENT DOCUMENTS

| | | |
|---|---|---|
| WO | WO-01/74419 A1 | 10/2001 |
| WO | WO-02/47751 A2 | 6/2002 |
| WO | WO-2011/039091 A1 | 4/2011 |

* cited by examiner

INTRAVASCULAR ROTARY BLOOD PUMP

RELATED APPLICATIONS

This application is the U.S. National Stage of International Application Number PCT/EP2013/058642, filed Apr. 25, 2013, which claims priority to German Patent Application No. 10 2012 207 049.4, filed Apr. 27, 2012. The entire contents of the foregoing applications are hereby incorporated herein by reference.

This invention relates to an intravascular rotary blood pump having one or more pressure sensors for measuring pressures within the patient's vascular system which are important for operating the blood pump and/or for assessing the patient's state of health.

Intravascular rotary blood pumps are used for temporary heart support and constitute an interesting alternative to conventional intraaortic balloon pumps (IABPs). Such blood pumps are introduced percutaneously into the femoral artery for example and guided through the body's vascular system in order to support or replace the pumping action in the heart, for example. U.S. Pat. No. 5,911,685 discloses an intravascular rotary blood pump possessing a pumping device and a catheter attached to the proximal end of the pumping device and having different lines, for example power supply lines for the pumping device, extending therethrough. The pumping device itself comprises a motor section and a pump section fastened to the distal end of the motor section. The pump section comprises a tubular pump housing with an impeller rotating therein which is seated on a motor shaft protruding out of the motor section. Extending from the distal end of the pump section is a flow cannula through which blood is sucked by the pumping device, or ejected thereby when the pumping direction is reversed, during operation of the blood pump. During operation, the pumping device protrudes with its flow cannula through a cardiac valve opening to enable blood to be pumped through the open cardiac valve by means of the pumping device. Furthermore, the blood pump is equipped with pressure sensors externally on the pump housing and externally on the flow cannula in order to establish the inlet pressure and the outlet pressure. Data regarding the inlet and outlet pressures, together with the power consumption of the electrical motor of the pumping device, form a set of relevant information for the function and delivery rate of the pumping device. In addition, the measured pressures enable inferences to be drawn about the positioning of the blood pump in the vascular system. Moreover, a comparison of the differential pressure with the current power consumption of the motor enables local states as well as cavitation and sucking to be ascertained.

EP 1 911 484 A2 presents different pressure-measuring systems finding employment with intraaortic balloon catheters, and points out their disadvantages. It is proposed therein to instead employ intraaortic balloon catheters with fiber-optic pressure sensors. The pressure-sensitive sensor head of the fiber-optic pressure sensor ends in a liquid-filled chamber which is sealed from the surroundings by a thin membrane. The thin membrane forms a part of the housing of the pumping device and transmits the surrounding pressure to the liquid within the chamber. The changing pressure within the chamber is detected by means of the pressure sensor. The position of the sensor head within the liquid-filled chamber sealed by the flexible membrane protects the pressure sensor against damage upon introduction and placement of the heart-support pump.

WO 2011/039091 A1 describes the employment of optical pressure sensors having optical waveguides in connection with an intravascular rotary blood pump. Here, too, a sensor head is located externally on the housing of the pump section. A second pressure sensor is configured as a separate pressure-measuring catheter which is laid through the actual catheter hose, exits from the catheter hose shortly before the pumping device and protrudes freely through the aortic valve well into the left ventricle. The optical pressure sensor described therein works on the Fabry-Perot principle and is also preferably employed in connection with the present invention. The sensor head of such a pressure sensor possesses a cavity which is terminated by a thin, pressure-sensitive glass membrane, on the one hand, and into which the end of an optical fiber protrudes, on the other hand. The pressure-sensitive glass membrane is deformed in dependence on the size of the pressure acting on the sensor head. Through the reflection on the glass membrane, the light exiting from the optical fiber is modulatingly reflected and fed into the optical fiber again. At the proximal end of the optical fiber there is located an evaluation unit having an integrated CCD camera, which evaluates the obtained light in the form of an interference pattern. In dependence thereon, a pressure-dependent electrical signal is generated.

However, other pressure sensors are also suitable in connection with the present invention, in particular fiber-optic pressure sensors of a different kind. Thus, for example U.S. Pat. No. 6,398,738 B1 describes both pressure sensors of the strain-gauge type, in particular on the basis of semiconductor materials such as silicon, and fiber-optic pressure sensors respectively for employment with intraaortic balloon catheters. It discusses, inter alia, a fiber-optic pressure sensor by which light is transmitted via a first fiber onto a mirror and the light reflected by the mirror is returned via a second fiber and evaluated. The mirror is part of a diaphragm which is exposed to the blood pressure on one side and to a reference pressure on the other side. However, a variant without the requirement of a reference pressure is in particular also explained.

The previously described pressure-measuring systems—in any case when applied in intravascular rotary blood pumps—do not always deliver sufficiently informative measuring data. In particular, high-frequency physiological pressure fluctuations cannot be distinguished unambiguously from spurious signals.

The object of the present invention is hence to improve the pressure measurement for intravascular rotary blood pumps.

This object is achieved by an intravascular rotary blood pump having the features of claim 1. Claims dependent thereon state advantageous embodiments and developments of the invention.

A preferred embodiment of an intravascular rotary blood pump according to the invention provides for this purpose for combining the pumping device fixed distally to the catheter with a pressure sensor by connecting a pressure-sensitive area of the pressure sensor to the pumping device so firmly that it is exposed to the surroundings whose pressure is to be measured, on the one hand, and is aligned orthogonally to a general longitudinal axis of the rotary blood pump, on the other hand.

It has turned out that a pressure sensor whose pressure-sensitive area firmly connected to the pumping device is aligned orthogonally to the blood pump's longitudinal axis enables high-frequency physiological signals up to 250 Hz to be derived from the signal data. Such information is of considerable importance for diagnosing a heart's state or recovery state. It is thought that the pressure measurements of conventional pressure sensors have superimposed thereon high-frequency spurious signals which come from unbalances and other dynamic influences during operation of the rotary blood pump. In particular, tests have shown that intravascular rotary blood pumps move back and forth in the radial direction, i.e. transversely to the general longitudinal axis, during operation. When the pressure-sensitive area of the pressure sensor is now aligned orthogonally to the longitudinal axis, as proposed, such transverse motions cause no compressive forces whatsoever on the pressure-sensitive area. Influences on the pressure-measuring result that are caused by the operation of the pumping device, in particular in the high-frequency range, are thus eliminated for the most part.

The pressure-sensitive area can be for example the glass membrane of the sensor head of the above-described pressure sensor working on the Fabry-Perot principle. However, if the sensor head itself only measures the pressure in a pressure chamber situated in front which is separated from the surroundings by a pressure-sensitive membrane for example, this membrane situated in front constitutes the pressure-sensitive area of the pressure sensor as intended by the present invention. For what matters is that pressure-transmitting area bordering directly on the surroundings whose pressure is to be measured.

As a pressure sensor there is preferably used an optical pressure sensor having an optical fiber in which the pressure-sensitive area is a membrane and the optical fiber ends at a distance from the membrane. Reference is made in this respect to the content of WO 2011/039091 A1. This means that the sensor head of the optical pressure sensor does not measure the pressure in a pressure chamber situated in front, but is exposed directly to the ambient pressure to be measured. The pressure sensor thereby responds faster and is not influenced by any oscillations that might build up in a pressure chamber situated in front. In particular, the pressure signal is not influenced by the medium in the pressure chamber. This can otherwise happen very easily through the influence of temperature and moisture.

It is further advantageous when there is used as a pressure-sensitive membrane a glass membrane ($SiO_2$) or ceramic membrane (e.g. $Si_3N_4$) which borders directly on the surroundings with its surface. The membrane has in particular no additional coating on its surface facing the surroundings, but has contact with the blood. Conventional membranes of this kind are polymer-coated, for example with silicone, and these coatings can swell and/or possess a different thermal expansion coefficient from the membrane itself. This causes stresses to be exerted on the membrane which lead to drift of the measuring result. By now employing a fully uncoated membrane as the pressure-sensitive area exposed to the surroundings, these disadvantages can be avoided and the measuring results accordingly improved further.

Depending on the pressure events to be measured, the rotary blood pump can be equipped with one, two, or more than two pressure sensors, which can be provided externally on the blood pump, for example at the proximal and/or at the distal end of the pumping device, and/or also within the pumping device, for example in a flow cannula.

Preferably, a first pressure sensor is fixed to a pump housing of the pumping device in which housing the impeller or, where applicable, a plurality of impellers of the rotary blood pump rotate. The pumping device possesses between the impeller and the catheter one or more blood flow-through openings in whose proximity the pressure-sensitive area is disposed, preferably distally of said blood flow-through openings. When the catheter is now advanced through a cardiac valve too far, the pressure sensor comes into the region of the cardiac valve before further advancing causes the blood flow-through openings to be closed by the cardiac valve. One notices immediately when the blood pump slides with its pump outlet (or inlet) into the region of the aortic valve. Besides the primary task of measuring physiological pressures that give information about the heart's state of health, this pressure sensor thus has the further function of correctly positioning the blood pump in the patient's vascular system. In this case, it can be exactly ensured in a pressure-based manner that the inlet openings are located in the heart chamber, and the outlet openings in the aorta. For this purpose, employing only one pressure sensor distally of the outlet openings, the modulation of the motor current of the pump is additionally considered when the pump is in operation and the heart is contracting. This results in a pulsating pump flow and consequently also a pulsating pump motor current when the inlet openings are positioned in the heart and the outlet openings are positioned in the aorta.

In addition or alternatively, a second pressure sensor is disposed at the distal end of the pumping device. The distal end of the pumping device normally consists of a flow cannula, having one or more further blood flow-through openings for blood to enter (or exit from) the pumping device. That is to say, blood is sucked (or ejected) by the pumping device through the flow cannula during operation of the blood pump. The pressure sensor can be disposed within the flow cannula to make it possible to identify for example that the flow cannula is being sucked against a heart chamber wall. But it is also important to have a pressure sensor externally on the flow cannula in proximity of its blood flow-through openings in order to measure the physiological pressure there. Thus, the ventricular pressure can be detected in a targeted manner with high time resolution (up to 250 Hz). There can be detected therefrom the heart recovery in the form of the cardiac contractility or the passive cardiac wall stress indirectly by measuring the relaxation rate (≈onset of diastolic filling phase) in the form of the pressure-based diastole. Moreover, there can be detected the end-diastolic filling pressures, so that blood can also be removed with the pump as required, avoiding high wall stresses at high end-diastolic pressures, which stand in the way of heart recovery.

If the sensor head of the pressure sensor or, in general terms, the distal end of the pressure sensor is fixed externally on the pumping device, e.g. externally on the pump housing or externally on the flow cannula, the pressure sensor is preferably guided along the pumping device externally from proximally to distally at least over a part of the pumping device up to a depression provided in the outer surface of the pumping device, in which depression the distal end of the pressure sensor is at least partly received. This protects the sensitive sensor head and in particular its pressure-sensitive membrane from colliding with a sluice valve or hemostatic valve when the blood pump is introduced into the patient's vascular system.

However, it may be that the wall thickness of the pumping device is not sufficient for producing a depression with a depth in which the sensor head can be completely received, so that the distal end of the pressure sensor projects radially beyond the periphery of the pumping device. In particular in such cases it is advantageous to provide distally before the sensor head a bulge likewise projecting beyond the periphery of the pumping device, in order to prevent the hemostatic valve or sluice valve from getting caught at the distal end of the pressure sensor when the blood pump is introduced into the patient's vascular system. It is particularly preferred in this connection to guide this bulge around the depression at least in a U shape or, where applicable, also completely in an O shape. This bulge can be formed for example by a bead of bonding agent, which might also only be applied after the sensor head has been fixed in the depression. The bulge, in particular the U-shaped bulge, can alternatively also be welded on or soldered on or be an integral part of the component.

Figure 2:
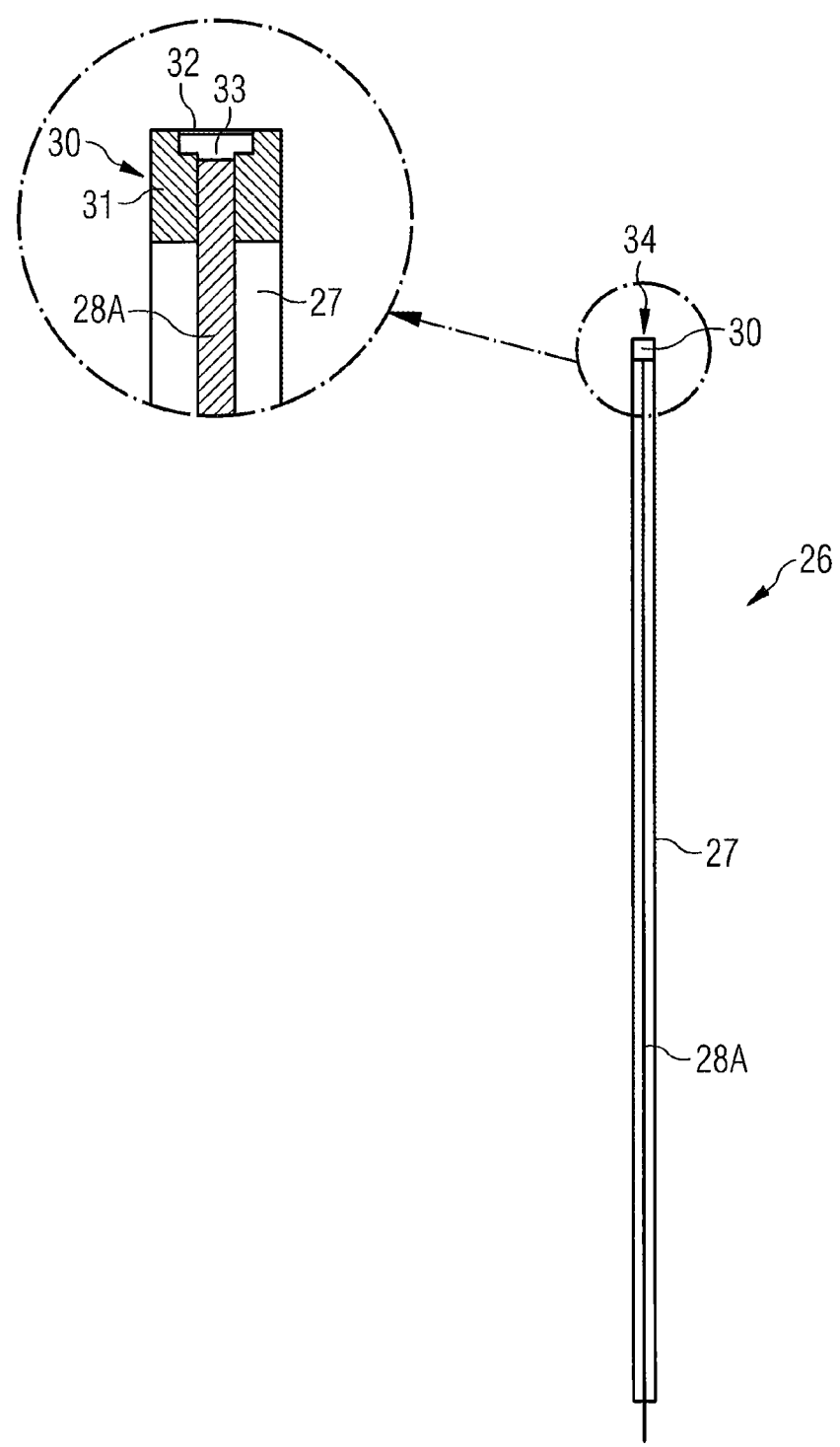
Figure 3:
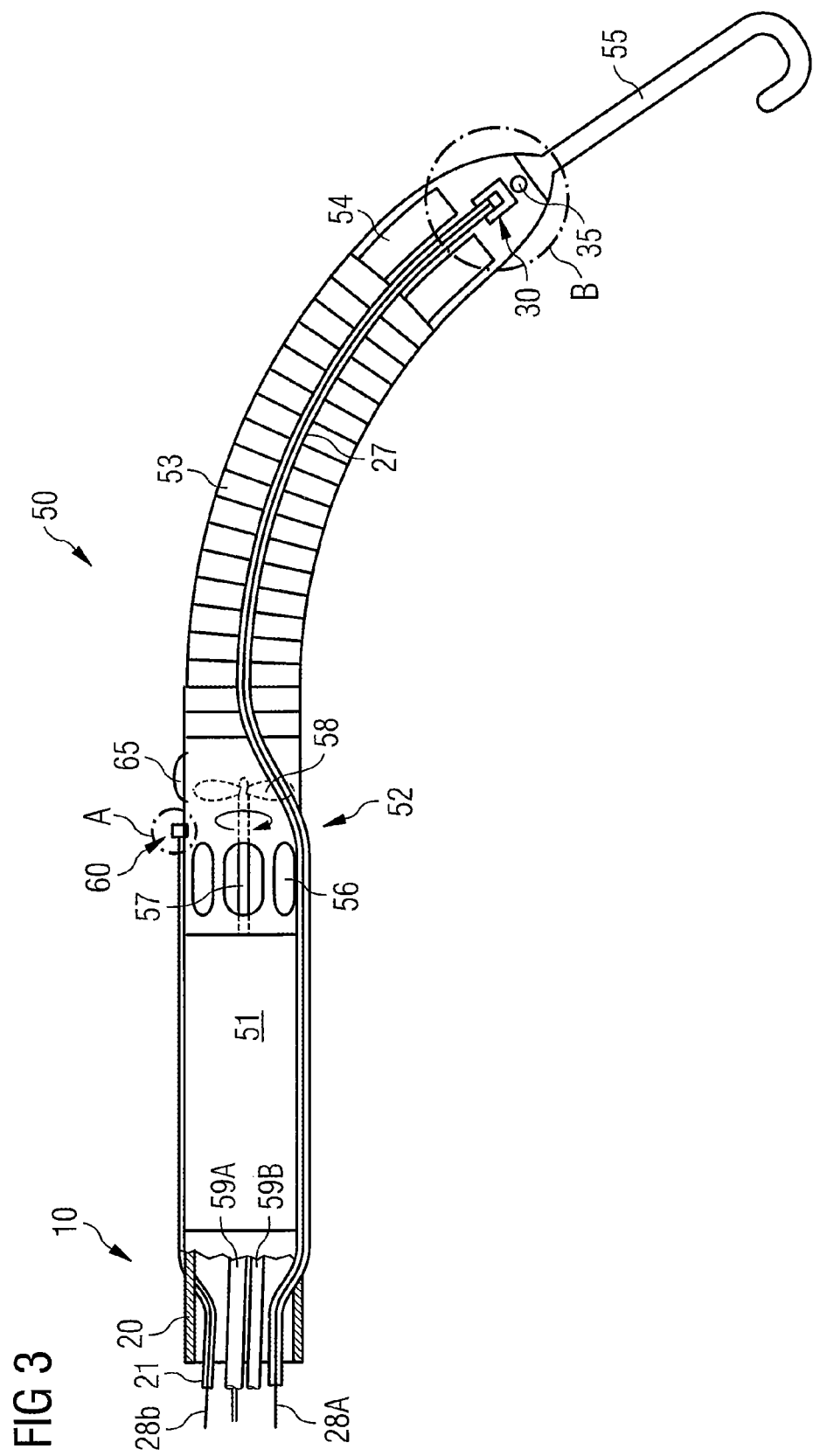
Figure 4A:
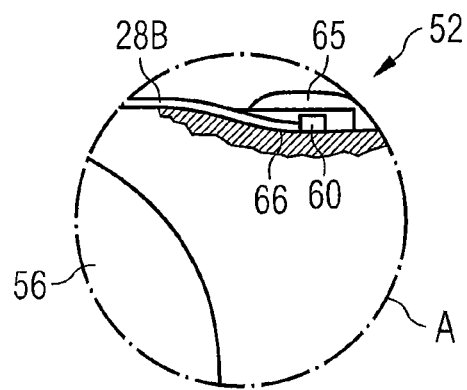
Figure 4B:
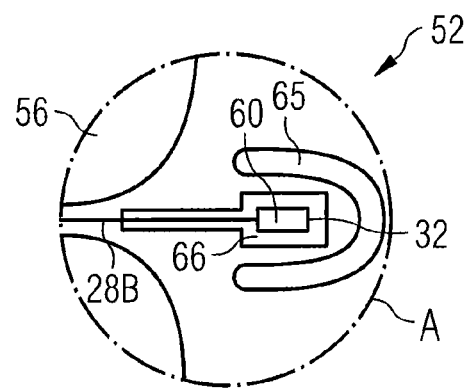
Figure 5A:
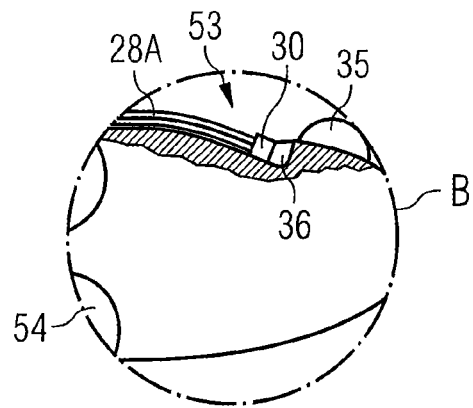
Figure 5B:
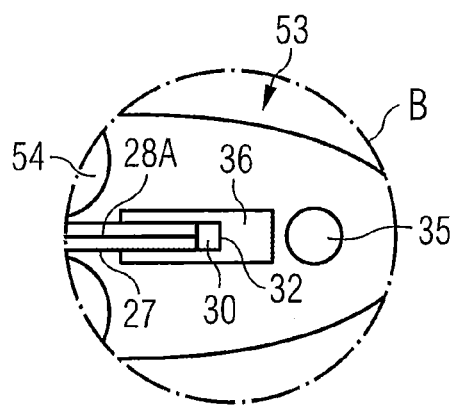

Hereinafter the invention will be explained by way of example with reference to the accompanying drawings. Therein are shown:

FIG. 1 a blood pump laid through the aorta, which extends through the aortic valve into the left ventricle and has an integrated pressure and kink sensor, FIG. 2 an optical pressure sensor having an optical fiber, FIG. 3 the pumping device of the blood pump from FIG. 1 in greater detail, FIGS. 4A, 4B the detail A from FIG. 3 in plan view and in side view, and FIGS. 5A, 5B the detail B from FIG. 3 in plan view and in side view.

FIG. 1 shows an intravascular blood pump having a catheter 10 which is introduced into the descending aorta 11 retrograde. The descending aorta is part of the aorta 12 which first ascends from the heart and then descends and has the aortic arch 14. At the beginning of the aorta 12 there is located the aortic valve 15 which connects the left ventricle 16 to the aorta 12 and through which the intravascular blood pump extends. The intravascular blood pump comprises in addition to the catheter 10 a rotary pumping device 50 fastened at the distal end of the catheter hose 20 and having a motor section 51 and a pump section 52 disposed at an axial distance therefrom, as well as a flow cannula 53 protruding in the distal direction from the inflow end of the pump section 52 and having a suction inlet 54 located at its end. Distally of the suction inlet 54 there is provided a soft-flexible tip 55, which can be configured for example as a "pigtail" or in a J shape. Through the catheter hose 20 there extend different lines and devices which are important for operating the pumping device 50. Of these, FIG. 1 only shows two optical fibers 28A, 28B which are attached at their proximal end to an evaluation device 100. These optical fibers 28A, 28B are respectively part of an optical pressure sensor whose sensor heads 30 and 60 are located externally on the housing of the pump section 52, on the one hand, and externally on the suction inlet 54, on the other hand. The pressure transmitted by the sensor heads 30 and 60 is converted into electrical signals in the evaluation device 100 and displayed e.g. on a display screen 101.

The measurement of both the aortic pressure by means of the sensor head 60 and the ventricular pressure by means of the sensor head 30 makes possible, in addition to the actual pressure signal, e.g. a contractility measurement by which the recovery of the heart is measured, as well as the establishment of the pressure difference which is used for computing the flow of the pumping device 50.

The principle of electro-optical pressure measurement will be explained more closely hereinafter with reference to FIG. 2. FIG. 2 shows a pressure-measuring catheter 26 having a lumen 27 in which an optical fiber 28A (which might also be a plurality of optical fibers or the optical fiber 28B) is freely movable. The lumen 27 can consist of a polymer, in particular polyurethane, or preferably of nitinol or another shape-memory alloy, exit from the catheter hose 20 at an exit point 57 (cf. FIG. 1) and be laid along the flexible flow cannula 53 e.g. externally. Within the catheter hose 20 the separate lumen 27 can be omitted. At the distal end 34 of the optical fiber 28A the pressure-measuring catheter has a sensor head 30 having a head housing 31 which contains a thin ceramic or glass membrane 32 which terminates a cavity 33. The membrane 32 is pressure-sensitive and is deformed in dependence on the size of a pressure acting on the sensor head 30. Through the reflection on the membrane the light exiting from the optical fiber 28A is reflected modulatingly and coupled back into the optical fiber. This does not require that the cavity 33 is terminated with the optical fiber 34. It can likewise be effected through the head housing 31. One must only make sure that the light is coupled in and out with low loss. At the proximal end of the optical fiber 28A, i.e. in the evaluation device 100, there is located a digital camera, e.g. a CCD camera or a CMOS, which evaluates the incoming light in the form of an interference pattern. In dependence thereon, a pressure-dependent electrical signal is generated. The evaluation of the optical image or optical pattern delivered by the camera and the computation of the pressure are effected by a computer attached to the camera, which also controls the power supply to the motor-operated pumping device 50 in dependence on the effected evaluation of the pressure signal.

Instead of the optical pressure sensor working on the Fabry-Perot principle as described with reference to FIG. 2, there can also be employed other pressure sensors, in particular optical pressure sensors having one or more optical fibers, as long as these other pressure sensors possess a pressure-sensitive area aligned orthogonally to the longitudinal axis of the pumping device 50 and exposed to the surroundings, for example a membrane or a diaphragm of a different kind.

The pumping device 50 from FIG. 1 is represented in further detail in FIG. 3. One can see a drive shaft 57 protruding from the motor section 51 into the pump section 52, which drives an impeller 58 by means of which, during operation of the blood pump, blood is sucked through the blood pass-through openings 54 at the distal end of the flexible flow cannula 53 and ejected proximally of the impeller 58 through the blood flow-through openings 56. The pumping device 50 can also pump in the reverse direction when it is adapted accordingly. Leading through the catheter hose 20 of the catheter 10 to the pumping device 50 are the above-mentioned optical fibers 28A, 28B, on the one hand, and a power-supply line 59A for the motor section 51 and a purge-fluid line 59B.

The sensor head 60 of the first pressure sensor is fixed externally on the pump housing of the pump section 52. The appurtenant optical fiber 28B is guided in a thin plastic hose 21 over a short distance of for example 5 cm within the catheter hose 20, in order to ensure that the optical fiber 28B does not break upon strong curvatures of the catheter 10 in this region of the catheter hose 20. Outside the pumping device 50 the optical fiber 28B is laid freely and only bonded to the outer wall of the pumping device 50 by means of bonding agent. This minimizes the outer cross-sectional dimensions of the pumping device 50. The bonding of the optical fiber 28B is possible because the pumping device 50 is rigid in this region and the optical fiber 28B hence does not have to be movable relative to the pumping device 50.

In contrast, the optical fiber 28A leading to the sensor head 30 of the second pressure sensor is laid freely in a hose or tubelet 17, preferably a nitinol tubelet, along the total periphery of the pumping device 50, so that it can shift relative to the pumping device 50 within said hose or tubelet upon changes of bend of the flow cannula 53.

The hose and/or tubelet 27 in which the optical fibers 28A, 28B are laid can extend slightly into the catheter hose 20, but can also extend completely through the catheter hose 20 and end in a corresponding plug at the end of the line for insertion of the relevant pressure sensor into a connection of the evaluation device 100. The optical fiber 28B as well as the optical fiber 28A are preferably glass fibers, which are usually polymer-coated for their isolation, for example with polyimide (Kapton).

Distally before the sensor heads 30 and 60 there is respectively provided a bulge 35, 65 which protects the sensor heads 30 and 60 from damage upon introduction of the blood pump through a hemostatic valve or sluice valve. Furthermore, the sensor heads 30 and 60 are respectively set in a depression 36, 66 of the pumping device 50. This is not represented in FIG. 3 and will be explained hereinafter with reference to FIGS. 4A, 4B and 5A, 5B.

FIG. 4A shows the detail A from FIG. 3 in greater detail and partly in cross section. FIG. 4B basically shows the same detail A, but in plan view from above. Thus, the sensor head 60 is received in a countersunk manner in a depression 66 provided on the outer surface of the pump section 52, the depression 66 being surrounded by a horseshoe- or U-shaped bulge 65. The bulge could also be closed into an O shape. It is bonded on or welded on, but can also form an integral part of the pump section 52. The optical fiber 28B is bonded on the surface and extends along a bar between two blood flow-through openings 56.

In a similar manner, the sensor head 30 of the second pressure sensor is also received in a countersunk manner in a depression 36 on the outer surface at the distal end of the flow cannula 53. Here, too, the nitinol tubelet 27 with the optical fiber 28A laid therein extends through over a bar between two blood flow-through openings 54. A point-shaped bulge 35 distally directly before the depression 36 protects the sensor head 30 from collision damage upon introduction of the blood pump. The bulge 35 can also be alternatively configured in a U shape or O shape and in particular be bonded on, welded on or an integral part of the flow cannula 53.

There can be seen in these two views according to FIGS. 4A, 4B and 5A, 5B the orthogonal alignment of the respective pressure-sensitive area or ceramic or glass membrane 32 relative to the longitudinal axis of the pumping device 50.

The sensor head 30 can alternatively extend together with the hose or tubelet 27 up to an arbitrary place on the soft-flexible tip 55 and be protected mechanically there e.g. by the walling of the soft-flexible tip 55. Bending-induced pressure artifacts are low, since the sensor membrane is disposed orthogonally to the walling. Only the bonded connection between the optical waveguide 34 and the sensor head 30 must be protected against bending. This can be effected through the tubelet 27 or an additional stiffening in the region of the bonding.

The invention claimed is:

1. An intravascular rotary blood pump, comprising:
a catheter;
a pumping device fixed distally to the catheter and having a longitudinal axis; and
a pressure sensor firmly connected to the pumping device, the pressure sensor comprising a pressure-sensitive area exposed to the surroundings and aligned orthogonally to the longitudinal axis of the pumping device.

2. The blood pump according to claim 1, wherein the pressure sensor is fixed to a pump housing of the pumping device in which housing at least one impeller rotates.

3. The blood pump according to claim 2, further comprising at least a first blood flow-through opening between the at least one impeller and the catheter, wherein the pressure sensor is so fixed to the pump housing that the pressure-sensitive area is disposed distally of and near the first blood flow-through opening.

4. The blood pump according to claim 1, wherein the pumping device has at its distal end a flow cannula having at least a second blood flow-through opening through which blood is either sucked or ejected by the pumping device during operation of the blood pump, wherein the pressure sensor is disposed near said second blood flow-through opening.

5. The blood pump according to claim 4, wherein the flow cannula has a soft-flexible tip distally of the second blood flow-through opening, and wherein a distal end of the pressure sensor is at least partly disposed in the soft-flexible tip.

6. The blood pump according to claim 1, wherein the pressure sensor is guided along the pumping device externally from proximally to distally, and wherein the pumping device has an outer surface having a depression in which a distal end of the pressure sensor is at least partly disposed.

7. The blood pump according to claim 1, wherein a distal end of the pressure sensor projects radially beyond the periphery of the pumping device, and wherein there is provided on the pumping device distally before said end of the pressure sensor a bulge likewise projecting beyond the periphery of the pumping device.

8. The blood pump according to claim 7, wherein the bulge is U-shaped or 0-shaped.

9. The blood pump according to claim 7, wherein the bulge is a bead of bonding agent.

10. The blood pump according to claim 7, wherein the bulge is welded or soldered on a surface of the pumping device.

11. The blood pump according to claim 7, wherein the bulge forms an integral part of the pumping device.

12. The blood pump according to claim 7, wherein the depression is surrounded by the bulge.

13. The blood pump according to claim 1, wherein the pressure sensor is an optical pressure sensor having an optical fiber, and wherein the pressure-sensitive area is a membrane and the optical fiber ends at a distance from the membrane.

14. The blood pump according to claim 1, wherein the pressure-sensitive area is a ceramic or glass membrane which is exposed directly to the surroundings with its ceramic or glass surface.

* * * * *